US008877187B2

(12) United States Patent
Schiltz et al.

(10) Patent No.: US 8,877,187 B2
(45) Date of Patent: *Nov. 4, 2014

(54) THERAPEUTIC ANTIBODIES FOR TREATMENT AND PROPHYLAXIS OF TRANSMITTABLE VIRAL DISEASES

(75) Inventors: James M. Schiltz, Sisseton, SD (US); Marshall K. Brinton, Spicer, MN (US); James K. Petell, Grand Forks, ND (US); David S. Bradley, Grand Forks, ND (US)

(73) Assignee: Avianax, LLC, Grand Forks, ND (US)

( * ) Notice: Subject to any disclaimer, the term of this patent is extended or adjusted under 35 U.S.C. 154(b) by 539 days.

This patent is subject to a terminal disclaimer.

(21) Appl. No.: 12/952,385

(22) Filed: Nov. 23, 2010

(65) Prior Publication Data

US 2011/0150904 A1    Jun. 23, 2011

Related U.S. Application Data

(63) Continuation-in-part of application No. 12/176,793, filed on Jul. 21, 2008, now Pat. No. 8,029,785, which is a continuation of application No. 11/459,832, filed on Jul. 25, 2006, now abandoned.

(60) Provisional application No. 60/595,652, filed on Jul. 25, 2005.

(51) Int. Cl.
| | | |
|---|---|---|
| *A61K 39/395* | (2006.01) | |
| *A61K 39/42* | (2006.01) | |
| *G01N 33/569* | (2006.01) | |
| *C07K 16/10* | (2006.01) | |
| *A61K 39/00* | (2006.01) | |

(52) U.S. Cl.
CPC ...... *C07K 16/1081* (2013.01); *G01N 33/56983* (2013.01); *C07K 2317/23* (2013.01); *G01N 2333/18* (2013.01); *G01N 2469/10* (2013.01); *A61K 2039/505* (2013.01); *G01N 2333/11* (2013.01)
USPC ............... 424/130.1; 424/159.1; 424/161.1

(58) Field of Classification Search
CPC ............... A61K 2039/505; A61K 2039/6056; C07K 16/18; C07K 16/02; C07K 2317/11; C07K 2317/23
See application file for complete search history.

(56) References Cited

U.S. PATENT DOCUMENTS

| | | |
|---|---|---|
| 3,316,153 A | 4/1967 | Van Frank |
| 3,627,873 A | 12/1971 | Moyer |
| 3,962,421 A | 6/1976 | Neurath |
| 4,000,257 A | 12/1976 | Cano |
| 4,724,210 A | 2/1988 | Oka et al. |
| 4,748,018 A | 5/1988 | Stolle et al. |
| 6,682,883 B1 | 1/2004 | Monath et al. |
| 2003/0211110 A1 | 11/2003 | Shimoni et al. |
| 2004/0009178 A1 | 1/2004 | Bowdish et al. |
| 2006/0057149 A1 | 3/2006 | Johnson et al. |
| 2006/0067940 A1 | 3/2006 | Diamond et al. |

FOREIGN PATENT DOCUMENTS

| | | |
|---|---|---|
| DE | 19504755 A1 | 8/1996 |
| EP | 152270 | 8/1985 |
| EP | 1371665 A1 | 12/2003 |
| EP | 1552848 A1 | 7/2005 |
| WO | WO-2004/026339 A1 | 4/2004 |
| WO | WO-2004/067035 A1 | 8/2004 |

OTHER PUBLICATIONS

Pletnev et al. Vaccine. Chimeric West Nile/dengue virus vaccine candidate: preclinical evaluation in mice, geese and monkeys for safety and immunogenicity. Vaccine. Sep. 29, 2006;24(40-41):6392-404. Epub Jun. 21, 2006.*
Agrawal et al., "Human Immunoglobulin as a Treatment for West Nile Virus Infection", *Journal of Infectious Diseases*, 2003, pp. 1-4, vol. 188, No. 1, Chicago, IL, U.S.A.
Austin et al., "An Outbreak of West Nile Virus-Associated Disease in Domestic Geese (*Anser anser domesticus*) upon Initial Introduction to a Geographic Region, with Evidence of Bird to Bird Transmission," *Can. Vet. J.*, 2004, vol. 45, pp. 117-123.
Banet-Noach et al., "(Non-Vector) Transmission of West Nile Virus in Geese," *Avian Pathol.*, Oct: 32(5): 489-94.
Behn et al.,"Use of Polyclonal Avian Antibodies" *Chicken Egg Yolk Antibodies, Production and Application*, 2001, pp. 108-210.
Ben-Nathan et al., "Prophylactic and Therapeutic Efficacy of Human Intravenous Immunoglobulin in Treating West Nile Virus Infection in Mice," *J Infect. Dis.*, 2003, vol. 188, pp. 5-12.
Berzofsky et al., "Progress on new vaccine strategies against chronic viral infections," *J Clin Invest*. Aug. 2004;114(4):450-62.
Brinton et al., "Immune Mediated and Inherited Defences Against Flaviviruses," *Clinical and Diagnostic Virology*, 1998, pp. 129-139, vol. 10.
Carlander, "Avian IgY Antibody: In Vitro and In Vivo," Acta Universitatis Upsaliensis, Comprehensive Summaries of Uppsala Dissertations from the Faculty of Medicine, Mar. 6, 2002 (published Ph.D. dissertation, Uppsala University).
Casadevall, "Passive Antibody Administration (Immediate Immunity) as a Specific Defense against Biological Weapons," *Emerging Infectious Diseases*, 2002, vol. 8(8), pp. 833-841.
Chung et al., "Antibodies against West Nile Virus Nonstructural Protein NS1 Prevent Lethal Infection through FC γ Receptor-Dependent and -Independent Mechanisms," *J. Virol.*, 2006, vol. 80(3), pp. 1340-1351.
Cohen, "Is an Effective HIV Vaccine Feasible," *Science*, vol. 30. p. 99 (2005).
Diamond et al., "A Critical Role for Induced IgM in the Protection against West Nile Virus Infection,"*J. Exp. Med.*, 2003, vol. 198(12), pp. 1853-1862.

(Continued)

*Primary Examiner* — Michelle S Horning
(74) *Attorney, Agent, or Firm* — Womble Carlyle Sandridge & Rice, LLC

(57) ABSTRACT

The invention provides methods and compositions for the treatment and prevention of a transmittable disease in a subject, such as avians and mammals. The methods and compositions of the invention specifically make use of avian antibodies to the disease to be treated or prevented. Administration of such avian antibodies to a subject has been shown effective for reducing mortality in a population of subjects that are infected, or become infected, with the disease. The invention also provides kits useful for detecting the presence of transmittable diseases in subjects.

13 Claims, No Drawings

(56) References Cited

OTHER PUBLICATIONS

Engle et al., "Antibody Prophylaxis and Therapy against West Nile Virus Infection in Wild-Type and Immunodeficient Mice," *J. Virol.*, 2003, vol. 77(24), pp. 12941-12949.
Gea-Banacloche et al., "West Nile Virus: Pathogenesis and Therapeutic Options," *Ann. Intern. Med.*, 2004, vol. 140(7), pp. 545-554.
Granwehr et al., "West Nile Virus: Where Are We Now?", *Lancet Infectious Diseases*, 2004, pp. 547-556, vol. 4, No. 9, U.S.A.
Haley et al., "The Role for Intravenous Immunoglobulin in the Treatment of West Nile Virus Encephalitis", 2003, pp. 88-90, vol. 37, No. 6, Bethesda, MD, U.S.A.
Huang et al., "Recent development o therapeutics for chronic HCV infection," *Antiviral Res* 71 (2006) 351-362.
Jackson, "Therapy of West Nile Virus Infection," *Can. J Neurol. Sci.*, 2004, vol. 31, pp. 131-134.
Koraka, "Detection of Immune-Complex-Dissociated Nonstructural-1 Antigen in Patients with Acute Dengue Virus Infections," *Journal of Clinical Microbiology*, 2003, pp. 4154-4159, vol. 41, No. 9.
Malkinson et al., "The assay of golsing hepatitis virus and antibody by spermagglutination and spermagglutination-inhibition," *Avian Pathology*. vol. 3, No. 3, p. 201-204 (1974).
Racanelli et al., "Presentation of HCV antigens to naive CD8+T cells: why the where, when, what and how are important for virus control and infection outcome," *Clin Immunol.* Jul. 2007;124(1):5-12.
Rollier et al. "Control of Heterologous Hepatitis C Virus Infection in Chimpanzees is Associated with the Quality of Vaccine-Induced Peripheral T-Helper Immune Response," *J Virol.* 2004, 78(1): 187-196.
Samina et al., "An Inactivated West Nile Virus Vaccine for Domestic Geese-Efficacy Study and a Summary of 4 Years of Field Application," Vaccine, 2005, pp. 4955-4958, vol. 23, Issue 41.p.
Srivastava et al. Neutralizing antibody responses to HIV: role in protective immunity and challenges for vaccine design. Expert Rev. Vaccines. 3(4) Suppl. 33-52 (2004).
Tesh et al., "Persistent West Nile Virus Infection in the Golden Hamster: Studies on Its Mechanism and Possible Implications for Other Flavivirus Infections," *J Infect. Dis.*, 2005, vol. 192, pp. 287-295.
Throsby et al., "Isolation and Characterization of Human Monoclonal Antibodies from Individuals Infected with West Nile Virus," *J. Virol.*, 2006, vol. 80(14), pp. 6982-6992.
Weingartl et al., "Comparison of Assays for the Detection of West Nile Virus Antibodies in Chicken Serum," *Canadian Journal of Veterinary Research*, 2003, pp. 128-132, vol. 47, No. 2.
Xiao et al., "West Nile Virus Infection in the Golden Hamster (*Mesocricetus auratus*): A Model for West Nile Encephalitis," *Emerging Infectious Diseases*, 2001, vol. 7(4), pp. 714-721.
Yang et al., "Plaque Reduction Test: an Alternative Method to Assess Specific Antibody Response to pIII-Displayed Peptide of Filamentous Phage M13," *J Immunol. Methods*, 2003, vol. 276, pp. 175-183.
Kris et al., "Passive Serum Antibody Causes Temporary Recovery From Influenza Virus Infection of the Nose, Trachea and Lung of Nude Mice," 1988, *Immunology*, pp. 349-353/.

\* cited by examiner

US 8,877,187 B2

THERAPEUTIC ANTIBODIES FOR TREATMENT AND PROPHYLAXIS OF TRANSMITTABLE VIRAL DISEASES

CROSS-REFERENCE TO RELATED APPLICATIONS

The present application is a continuation-in part of U.S. patent application Ser. No. 12/176,793, filed Jul. 21, 2008 now U.S. Pat. No. 8,029,785, which is a continuation of U.S. patent application Ser. No. 11/459,832, filed Jul. 25, 2006 (now abandoned), which claims priority to Provisional Patent Application Ser. No. 60/595,652, filed Jul. 25, 2005, all of which are incorporated herein by reference in their entirety.

FIELD OF THE INVENTION

The present invention is directed to compositions and the use thereof in the treatment and prevention of transmittable diseases, and particularly viral diseases. The compositions incorporate serum comprising avian antibodies against the transmittable disease, and the compositions can be used in a variety of subjects, including avians and mammals.

BACKGROUND

Previously known approaches to dealing with epidemiological outbreaks of transmittable clinical diseases have traditionally focused on three approaches: isolation of affected individuals; use of antimicrobial agents, and use of vaccinations. Antimicrobial agents have been used successfully for treatment once the pathogen has been identified; however, if the microorganism is resistant to the antimicrobial agent, there are limited or no options other than relying on the patient's own immune system for recovery or survival (in the case of life-threatening infections).

Individuals have been routinely protected by vaccinating, or immunizing, against an attenuated bacterial or viral strain where the vaccine has demonstrated good efficacy in prior tests. The underlying flaws of vaccinations are its safety, lack of protection against diverse strains causing the disease, availability of sufficient supplies of the vaccine, and most importantly, administration of the vaccine in sufficient time prior to infection to elicit an immune response in the patient against the pathogen. Unfortunately, in the event that the population is not vaccinated by the time an outbreak reaches epidemic proportions, a vaccination program that requires multiple injections over a significant period of time would have very limited effectiveness in protecting the population. In addition, individuals having impaired immunity (i.e., are immunodeficient) would be unable to generate an effective response. Moreover, given the high cost of a broad vaccination program, the general population has been vaccinated to only a limited number of pathogens. The rise of numerous emerging infectious diseases and the threat of bioterrorism acts have significantly elevated the susceptibility of large populations to a potentially epidemic disease outbreak.

Another approach, which has been referred to as "passive therapeutic immunity," to dealing with infection is the use of therapeutic antibodies for the treatment of pathogenic agents that are incurable by antimicrobial agents. Passive therapeutic immunity may also be used for individuals who have not been previously vaccinated. For example, the use of therapeutic antibodies has been reported with different degrees of protection against anthrax, biological toxins, brucellosis, Q fever, plague, smallpox, tularemia, viral encephalitides, and viral hemorrhagic fevers. Recent work has focused on the use of monoclonal antibodies, particularly because they can be produced in cell culture in large quantities once the hybridoma cell line is isolated. Alternatively, a recombinant mouse monoclonal antibody can be engineered with human sequences (generally referred to as a "humanized antibody") and produced in large quantities, albeit at expensive costs that may be prohibitory for broad use.

A severe drawback of the use of monoclonal antibodies is that they recognize only a single site or epitope on the microorganism, which is not as effective as polyclonal antibodies that recognize multiple sites. For example, previous testing using anthrax polyclonal sera containing antibodies to several sites demonstrated protective efficacy of the polyclonal antibodies. However, when the same test was performed using monoclonal antibodies, only one of four monoclonal antibodies tested conferred protection. Another limitation of monoclonal antibody treatment is that monoclonal antibodies offer limited protection to pathogens where the epitope is not conservatively maintained, such as a pathogen having numerous species or viral pathogens that prone to a higher mutation frequency.

West Nile Virus is a specific example of a disease where treatment after contacting the disease shows little efficacy. Specifically, it is recognized in the art that there is not yet any experimental evidence that therapy with immunoglobulin will improve survival or neurological outcome of experimental animals when this therapy is initiated after the development of the clinical neurological disease. Further, no studies, either prophylactic for protection or post-infection for therapy, have demonstrated effectiveness of immunoglobulin treatment in animals that become infected by natural transmission of West Nile Virus.

Published U.S. Patent Application 2003/0211110 to Shimoni et al. discloses that hyperimmune sera collected from humans was able to facilitate the recovery of two immunocompromised patients tested positive by West Nile Virus upon continuous treatment with antibody delivered intravenously. In a separate report by Jackson, Can. J. Neurol. Sci., 2004, however, a patient showed no beneficial effect upon similar treatment. It is therefore unclear whether the specified treatment alone was responsible for the recovery of the patients, and more so, if immunosuppression was a key factor required for treatment.

In light of the above, it is clear that further, more effective methods of treating and preventing infection, particularly by a transmittable viral disease, are needed. The present invention provides pharmaceutical compositions and methods of preparation and use thereof that are particularly beneficial for treating and preventing such infection.

SUMMARY OF THE INVENTION

The present invention relates to the use of avian antibodies, particularly goose antibodies, for treating and preventing infection in a subject by a transmittable viral disease. As such, the invention can provide specific compositions that are useful in treatment as described herein, and the invention also can provide specific methods of treatment as described herein. In particular embodiments, the invention is specifically useful for reducing mortality in mammals that become infected or are infected with a transmittable viral disease. The invention can be practiced in relation to any mammal, particularly humans.

In certain embodiments, the invention particularly can provide methods of treating a mammal infected with a virus in the Flaviviridae family, particularly a virus in the flavivirus genus. Specifically, the methods can comprise administering to the mammal an amount of a serum comprising polyclonal goose antibodies against a virus in the Flaviviridae family. In further embodiments, antibodies from other avians also can be useful according to the invention, such as chicken antibodies.

In specific embodiments, the polyclonal goose antibodies can be antibodies against the very same virus that is infecting the mammal being treated according to the invention. The present invention, however, also can provide for treatment wherein the polyclonal goose antibodies are antibodies against a first virus in the Flaviviridae family (or specifically the flavivirus genus) and the virus infecting the mammal is a second, different virus in the Flaviviridae family (or specifically the flavivirus genus). Thus, the invention can provide for intra-family or intra-genus treatment (i.e., antibodies against one virus in a family or genus being effective for treatment of infection by a different virus in the same family or genus). In certain embodiments, the invention particularly can relate to treatment or prophylaxis of infection by a flavivirus in the mammalian tick-borne virus group, the seabird tick-borne virus group, the Aroa virus group, the Dengue virus group, the Japanese encephalitis virus group, the Kokobera virus group, the Ntaya virus group, the Spondweni virus group, the Yellow fever virus group, the Entebbe virus group, the Modoc virus group, or the Rio Bravo virus group.

In other embodiments, the invention particularly can provide methods of treating a mammal infected with an influenza virus. Specifically, the methods can comprise administering to the mammal an amount of a serum comprising polyclonal goose antibodies against an influenza virus. In further embodiments, antibodies from other avians also can be useful according to the invention.

In specific embodiments, the polyclonal goose antibodies can be antibodies against the very same influenza virus that is infecting the mammal being treated according to the invention. The present invention, however, also can provide for treatment wherein the polyclonal goose antibodies are antibodies against a first influenza virus (or specifically a virus of the influenzavirus A type) and the virus infecting the mammal is a second, different influenza virus (or specifically a virus of the influenzavirus A type). In certain embodiments, the invention particularly can relate to treatment or prophylaxis of infection by a human influenza virus, an avian influenza virus, a swine influenza virus, an equine influenza virus, a canine influenza, or a cat influenza virus.

In further embodiments, the invention can provide methods of treating a mammal infected with a virus in a variety of further virus families. Viruses in any of the viral families disclosed herein that affect mammals, particularly humans, can be encompassed by the methods and compositions of the present invention.

In some embodiments, the serum used in the compositions and methods of the invention can be particularly characterized by its surprisingly high neutralization titer as evaluated according to a plaque reduction test. In preferred embodiments, a serum comprising polyclonal goose antibodies (or other avian antibodies) can exhibit a neutralization titer of at least about 1:500, at least about 1:1000, or even greater, as otherwise described herein.

The invention further can be particularly characterized by the ability to provide treatment without the requirement of initial actions to prepare a subject for treatment. For example, the invention particularly can be used in embodiments wherein the mammal being treated with goose antibodies has not been de-sensitized to goose antibodies prior to carrying out the invention (i.e., by administering a serum comprising the polyclonal goose antibodies against the virus).

In other embodiments, the invention particularly can relate to a pharmaceutical composition. For example, such composition can comprise a serum effective for treatment or prophylaxis of a viral infection in a mammal arising from a virus in the Flaviviridae family. In such embodiments, the serum preferably can comprise polyclonal goose antibodies against a virus in the Flaviviridae family. In particular, the serum can exhibit a neutralization titer for the antibodies of at least about 1:500 when evaluated according to a plaque reduction test. In another example, a composition according to the invention can comprise a serum effective for treatment or prophylaxis of a viral infection in a mammal arising from an influenza virus. In such embodiments, the serum preferably can comprise polyclonal goose antibodies against an influenza virus. In particular, the serum can exhibit a neutralization titer for the antibodies of at least about 1:500 when evaluated according to a plaque reduction test. Compositions according to the invention can comprise additional components in addition to the noted serum. For example, the compositions may comprise a pharmaceutically acceptable carrier. Likewise, the compositions may be provided in kits wherein the composition can be provided in a specific unit volume (e.g., in a vial). Such kits could comprise multiple containers (or vials) of the composition, as well as further components, such s instructions for administration of the composition and/or dilutions suitable for providing multiple dosings of the composition.

DETAILED DESCRIPTION OF THE INVENTION

The present inventions now will be described more fully hereinafter with reference to specific embodiments of the invention and particularly to the various drawing provided herewith. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

In describing the present invention, various terms and phrases may be used herein, and such terms and phrases will have the same meaning thought the specification.

"Serum" means any fraction of blood serum that contains antibodies and one or more further protein blood components, said protein blood components comprising at least 30% by weight of the serum.

"Polyclonal antibodies" means a fraction of antibodies isolated from a host, the fraction comprising at least 80% of the total group of different antibodies produced by different immune cells in the host having affinity for different antigens on a virus.

"Neutralization titer" means quantification of an antibody that prevents or treats viral infection and subsequent detrimental viral effects, including cell death, in vitro, such as cell cultures including plaque assays, or in vivo, such as animal testing and clinical treatment. Antibodies that are shown present in a sample by ELISA, Western analyses, or like methods may or may not exhibit a neutralization titer.

"Natural transmission" means the transmission of an indigenous transmittable viral disease that occurs as a result of one or more animals being infected in an environment where the animal is freely exposed to carriers of the transmittable viral disease.

"Naturally occurring strain" or "indigenous strain" means a viral strain that is present in the natural environment and not having been reproduced in a laboratory.

"Attenuated" means a viral strain that has been weakened or made less virulent.

"Gosling" means any goose that has not reached maturity in terms of reaching a breeding age.

The treatment of human patients with mammalian antibodies is known to cause strong immunoreactions in non-immunosuppressed human patients. The treatment of human patient with non-human, mammalian antibodies likewise can cause strong immunoreactions. For example, administration of horse antivenin can produce side effects in humans such as severe allergic reactions, and, in extreme cases, death. Therefore, in the ever-increasing need for effective treatment and prevention of disease, particularly in relation to viral diseases, an alternative to mammalian antibodies is needed.

Avians are one potential source for antibodies with reduced risk of immunoreaction. Even then, the prior art has suggested that desensitization is required for cross-species antibody therapies. The present invention has found, however, that avian antibodies from specific sources can exhibit fewer or no side effects because they do not activate mammalian complement systems, bind to mammalian rheumatoid factors, naturally occurring anti-mammalian antibodies, or mammalian Fc receptors. The present invention thus realizes the ability to use antibodies from specific avian sources to treat or prevent infection by a transmittable viral disease in other avians and mammals.

According to the present invention, it has been found that avian therapeutic antibodies can be an effective means to protect and treat a population of birds in the field by delivery of an effective dose of the therapeutic antibodies. Moreover, it has been found that avian therapeutic antibodies can also be an effective means to protect and treat mammals.

In certain embodiments, the present invention thus provides methods of treating subjects by administering to the subjects avian antibodies against a transmittable viral disease. Advantageously, in specific embodiments, the present invention allows for treatment wherein the subject being treated has not been de-sensitized to the avian (e.g., goose) antibodies prior to treatment via administration of the antibodies. In other words, it can be understood that the subject being treated has not been fed or otherwise administered compositions containing avian (e.g., goose) antibodies, particularly for the purpose of achieving de-sensitization, prior to treatment by administering the antibodies against the transmittable viral disease. Thus, in methods of treatment according to the invention, treatment may expressly exclude any step related to de-sensitization of the subject (i.e., mammal) prior to administration of the avian antibodies against the transmittable viral disease.

In specific embodiments, the avian antibodies are goose antibodies. For simplicity, the invention may be described herein in relation to geese and goose antibodies. It is understood, however, that one of skill in the art armed with the present disclosure may be capable of extending the present invention in relation to further avians and avian antibodies, and such are believed to be encompassed by the present invention. In particular, the present invention should be recognized as relating to antibodies obtained, in certain embodiments, from other waterfowl, such as ducks, or from turkeys or ostriches. In still further embodiments, the invention may be related to antibodies derived from chickens.

Therefore, according to various embodiments of the present invention, there are provided compositions and methods of use thereof for treating or preventing infection in a subject by a transmittable viral disease. The invention is particularly characterized by the realization of the therapeutic ability of high neutralization titer serum to a transmittable viral disease collected from animals that were naturally infected with the transmittable viral disease. Alternatively, high neutralization titer sera may be produced by immunization with an attenuated strain of a transmittable viral disease.

Treatment and prevention, according to the invention, are particularly evidenced by a reduction in the mortality rate in a population of subjects to which the serum is administered. Previous attempts to affect treatment of so-called "previously un-curable diseases" have been limited to alleviation or amelioration of symptom associated with the disease. Moreover, while such previous attempts have alleged prolonging the survival of infected subjects, such attempts have specifically failed to evidence actual reduction in the mortality of previously infected subjects. Even more particularly, there has been no evidence provided heretofore of any methods of preventing infection through use of goose antibodies and subsequently reducing mortality in a population at risk for infection by a transmittable viral disease. According to the present invention, there are provided methods of reducing mortality in a population of subjects by both treatment and prophylaxis through use of goose antibodies.

In addition to reducing mortality in a population of subjects, treatment according to the present invention can be understood to relate to lessening or complete cessation of one or more symptoms associated with the transmittable viral disease. Treatment can also include avoiding worsening of symptoms present at the time of first treatment and avoiding occurrence of further symptoms not present at the time of first treatment. Accordingly, in one embodiment, treatment can be effected through preventing or limiting one or more symptoms associated with infection by the transmittable viral disease.

Prevention of infection according to the present invention does not necessarily mean completely preventing a subject from contracting a transmittable viral disease. Rather, a subject could contract the disease after administration of the composition of the invention such that testing would indicate the presence of the virus in the subject, but the subject could be completely free of symptoms associated with the disease. In such a case, even though a subject could test positive for the disease, the absence of symptoms associated with the disease would indicate prevention. Accordingly, in one embodiment, the invention is directed to a method of preventing active infection in a subject. Prevention could also be evidenced by a reduction in mortality in a population of subjects to which the composition of the invention has been administered. In such a case, reduced mortality, when compared to a population not subject to administration of the inventive composition, would be indicative of prevention according to the invention. Preferably, prevention means complete absence of infection in a subject to which the composition of the invention has been administered.

The present invention is particularly directed to methods and compositions for treatment of transmittable viral diseases. As such, the invention is capable of use in the treatment or prevention of a variety of viral diseases. In some embodiments, the invention can be described as relating to treatment or prevention of a viral disease that is recognized as being treated, treatable, prevented, or preventable by administration of antibodies against the transmittable viral disease.

In particular embodiments, the invention relates to treatment or prevention of infection by viruses in the family Flaviviridae. In further embodiments, the invention relates to treatment or prevention of infection by viruses in a specific genus encompassed by the Flaviviridae family. For example, the invention can relate to treatment or prevention of infection by viruses in the genus flavivirus. Flaviviruses share a common size (i.e., about 40-65 nm), symmetry (i.e., enveloped, icosahedral nucleocapsid), and nucleic acid structure (i.e., positive-sense, single stranded RNA having approximately 10,000-11,000 bases). Flaviviruses have a (+) sense RNA genome and replicate in the cytoplasm of the host cells. The genome mimics the cellular mRNA molecule in all aspects except for the absence of the poly-adenylated (poly-A) tail. This feature allows the virus to exploit cellular apparatus to synthesize both structural and non-structural proteins during replication. The cellular ribosome is crucial to the replication of the flavivirus, as it translates the RNA, in a similar fashion to cellular mRNA, resulting in the synthesis of a single polyprotein. The (+) sense RNA genome of Flavivirus contain 5' and 3' untranslated regions (UTRs). The 3' UTRs are typically 0.3-0.5 kb in length and contain a number of highly conserved secondary structures common to the flavivirus family. The present invention encompasses treatment related to tick-borne flaviviruses, mosquito-borne flaviviruses, and flaviviruses with no known arthropod vector. Specifically, the present invention encompasses treatment of flaviviruses, such as Gadgets Gully virus, Kadam virus, Kyasanur Forest disease virus, Langat virus, Omsk hemorrhagic fever virus, Powassan virus, Royal Farm virus, Tick-borne encephalitis virus, Louping ill virus, Meaban virus, Saumarez Reef virus, Tyuleniy virus, Aroa virus, Dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokovera virus, Bagaza virus, Ilheus virus, Israel turkey meningoencephalomyelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, Yellow fever virus, Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, and Rio Bravo virus.

In further embodiments, the invention can relate to treatment or prevention of infection by viruses in the family Orthomyxoviridae. In specific embodiments, the invention relates to treatment or prevention of infection by viruses in a specific genus encompassed by the Orthomyxoviridae. For example, the invention can relate to treatment or prevention by viruses in the genera influenzavirus A, influenzavirus B, or influenzavirus C. The term "influenza virus" as used herein can encompass viruses in any of the above-noted influenzavirus genera.

Influenzaviruses A, B and C are very similar in overall structure. The virus particle is 80-120 nanometers in diameter and usually roughly spherical, although filamentous forms can occur (more commonly in influenza C), which can form cordlike structures up to 500 microns long on the surfaces of infected cells. Despite these varied shapes, the viral particles of all influenza viruses are similar in composition. These are made of a viral envelope containing two main types of glycoproteins wrapped around a central core containing the viral RNA genome and other viral proteins that package and protect this RNA. RNA tends to be single stranded but in special cases it is double stranded. The present invention encompasses treatment related to various types of influenza viruses, including human influenza (or human flu), avian influenza (or bird flu), swine influenza, equine influenza, canine influenza, and cat flu. Hemagglutinin (HA) and neuraminidase (NA) are the two large glycoproteins on the outside of influenza viral particles. HA is a lectin that mediates binding of the virus to target cells and entry of the viral genome into the target cell, while NA is involved in the release of progeny virus from infected cells, by cleaving sugars that bind the mature viral particles. These proteins are targets for antiviral drugs, and they are antigens to which antibodies can be raised. Influenza A viruses are classified into subtypes based on antibody responses to HA and NA. These different types of HA and NA form the basis of the H and N distinctions. The present invention encompasses treatment of influenza viruses having any recognized H and N classification. For example, the present invention encompasses treatment of influenza viruses classified as H1N1, H1N2, H1N7, H2N2, H3N1, H3N2, H3N8, H4N8, H5N1, H5N2, H5N8, H5N9, H6N2, H6N5, H7N1, H7N2, H7N3, H7N4, H7N7, H8N4, H9N2, H10N7, H11N6, H12N5, H13N6, and H14N5.

In other embodiments, the invention can relate to treatment or prevention of infection by a variety of further viral diseases. For example, the invention can relate to treatment or prevention of infection from viruses of the family Herpesviridae. More specifically, the virus may be of one of the following genera: Iltovirus, Mardivirus, Simplexvirus, Varicellovirus, Cytomegalovirus, Muromegalovirus, Proboscivirus, Roselovirus, Lymphocryptovirus, Macavirus, Percavirus, and Rhadinovirus. In specific embodiments, the viral disease that can be treated or prevented according to the invention can comprise herpes simplex virus 1 (HSV-1), herpes simplex virus 2 (HSV-2), varicella zoster virus (VZV), Eppstein-Barr virus, cytomegalovirus, roseolovirus, and Kaposi's sarcoma-associated herpesvirus (KSHV).

In further embodiments, the invention can relate to treatment or prevention of infection from viruses of the family Paramyxoviridae. More specifically, the virus may be of one of the following genera: Avulavirus (e.g., Newcastle disease virus), Henipavirus (e.g., Hendravirus and Nipahvirus), Morbillivuris (e.g., Measles virus, Rinderpest virus, Canine distemper virus, Phocine distemper virus, Peste des Petits ruminants virus), Respirovirus (e.g., Sendai virus, Human Parainfluenza viruses, and common cold viruses), Rubulavirus (e.g., Mumps virus, Human Parainfluenza viruses, Simian Parainfluenza viruses, Menangle virus, Tioman virus, and Tuhokoviruses), Pneumovirus (e.g., Human Respiratory Syncytial virus, and Bovine Respiratory Syncytial virus), Metapneumovirus (e.g., Avian Pneumoirus and Human Metapneumovirus), Fer-de-Lance virus, Nariva virus, Tupaia Paramyxovirus, Salem virus, J virus, Mossman virus, and Beilong virus.

In other embodiments, the invention can relate to treatment or prevention of infection from viruses of the family Rhabdoviridae. More specifically, the virus may be of one of the following genera: Cytorhabdovirus (e.g., Lettuce necrotic yellows virus), Dichorhabdovirus (e.g., Orchid fleck virus), Ephemerovirus (e.g., Bovine ephemeral fever virus), Lyssavirus (e.g., Rabies virus), Novirhabdovirus (e.g., Infectious Hematopoietic necrosis virus), Nucleorhabdovirus (e.g., Potato yellow dwarf virus), and Vesiculovirus (e.g., Vesicular stomatitis virus).

In certain embodiments, the invention can relate to treatment or prevention of encephalitis arising from viral infections. For example, the encephalitis treated or prevented according to the invention may be encephalitis arising from one or more of Herpes simplex, Varicella zoster virus, Rabies, HIV, and H5N1. In further examples, the invention can relate to treatment or prevention of an Arbovirus encephalitis (e.g., La Crosse encephalitis, California encephalitis virus, Japanese encephalitis, St. Louis encephalitis, Equine encephalitis, Murray Valley encephalitis, Tick-borne meningoencephalitis, Powassan encephalitis, and encephalitis arising from West Nile virus). Other viral encephalitides that can be treated or prevented according to the invention include Eastern equine encephalomyelitis virus, Venezuelan equine encephalomyelitis virus, and Western equine encephalomyelitis virus.

In other embodiments, the invention can relate to treatment or prevention of conditions recognized as viral hemorrhagic fevers (such as Ebola, Marbug, Junin, Argentine, and Lassa). In certain embodiments, the invention thus can relate to treatment or prevention of infection from viruses of the family Arenaviridae, Filoviridae, Bunyaviridae, and Flaviviridae (which is already described above).

In relation to the family Arenaviridae, the virus may be of one of the following genera: Ippy virus, Lujo virus, Lymphocytic choriomeningitis virus, Mobala virus, Mopeia virus, Amapari virus, Chapare virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, and Whitewater Arroyo virus. In relation to the family Filoviridae, the virus may be of the Marburgvirus genus or the Ebolavirus genus. More specifically, the virus may include Zaire virus, Sudan ebolavirus, Reston ebolavirus, Cote d'Ivoire ebolavirus (also known as Ivory Coast ebolavirus and Tai ebolavirus, and Bundibugyo ebolavirus. In relation to the family Bunyaviridae, the virus may be of one of the following genera: Hantavirus (e.g., Hantaan virus), Nairovirus (e.g., Dugbe virus), Orthobunyavirus (e.g., Bunyamwera virus), and Phlebovirus (e.g., Rift Valley fever virus).

In specific embodiments, non-limiting examples of further viral diseases that can be treated or prevented according to the invention include Hepatitis A, Hepatitis B, Ectocarpus Siliculosus Virus, and any other viral diseases that are amenable to treatment and/or prevention via administration of antibodies. In some embodiments, the invention can even relate to treatment or prevention of infection by diseases not previously recognized as being easily treated or prevented, such as Hepatitis C and Human Immunodeficiency Virus.

In other embodiments, the invention can be characterized as providing for treatment or prevention of infection by viruses recognized as RNA viruses. In specific embodiments, the methods and compositions of the invention may be used in the treatment or prevention of viral diseases classified in any of the following families: Birnaviridae, Reoviridae (including Rotavirus), Coronaviridae [including Coronavirus and Severe Acute Respiratory Syndrome (SARS)], Picornaviridae (including Poliovirus, the common cold virus, and Hepatitis A virus), Astroviridae, Caliciviridae (including Norwalk virus), Flaviviridae (as described above), Rhabdaviridae (including Rabies virus), Togaviridae (including Rubella virus, Ross River virus, Sindbis virus, and Chikungunya virus), Bornaviridae (including Borna disease virus), Filoviridae, Paramyxoviridae, Arenaviridae, Bunyaviridae, and Orthomyxoviridae. Such classification also includes viruses of the genus Hepevirus (including Hepatitis E virus), Deltavirus, and Nyavirus.

In other embodiments, the invention can be characterized as providing for treatment or prevention of infection by viruses recognized as DNA viruses. In specific embodiments, the methods and compositions of the invention may be used in the treatment or prevention of viral diseases classified in any of the following families: Myoviridae, Podoviridae, Adenoviridae, Asfarviridae, Herpesveridae, Hepadnaviridae, Papillomaviridae, Polyomaviridae, Poxviridae, Anelloviridae, and Parvoviridae.

In still further embodiments, the invention can be characterized as providing for treatment or prevention of infection by viral agents that are cancer-causing viruses. Thus, the invention can be directed to treatment or prevention of viral oncogenes. Non-limiting examples of such viruses include human papillomavirus, Hepatitis B, Hepatitis C, Epstein-Barr virus, Human T-lymphotropic virus, Kaposi's sarcoma-associated herpesvirus, Merkel cell polyomavirus, Compositions for use according to the invention can comprise goose serum comprising antibodies to the specific viral disease. Such serum can be obtained or prepared by a variety of methods, and the serum can include a variety of components. As previously noted, the serum comprises goose antibodies to the disease for which treatment or prevention is desired. The goose antibodies can be present naturally in the serum or can be incorporated into the serum as desired in the preparation of the serum.

In one preferred embodiment, the avian antibodies are naturally present in the serum as obtained from a host. Accordingly, it is preferred for the serum to comprise sera collected from one or more avian hosts. Preferably, the sera are collected from at least two avian hosts. In specific embodiments, as noted previously, the avian host can be a goose. Therefore, preparation of the inventive composition may be further described herein in reference to obtaining sera from geese. Of course, the invention also encompasses embodiments wherein the sera is obtained from further avians including, but not limited to ducks, turkeys, ostriches, chickens, and any further avians recognizable by one of skill in the art as being useful in light of the further disclosure provided herein.

Preferably, those avians of the biological family Anatidae, or commonly known as waterfowl, are preferred over other avian species. For example, the current highly pathogenic avian influenza (HPAI), H5N1, exhibits very high mortality, approaching or at 100%, to chickens and turkeys. In contrast, waterfowl birds can be carriers of the H5N1 strain. In fact, various H5N1 strain variants can cause substantially reduced or no mortality in domestic waterfowl relative that observed in chickens. The resistance of waterfowl is predicted to be due to the immunological system, and specifically antibodies, of the genus.

The avian hosts (e.g., geese) used for collecting the sera are preferentially geese that have been infected by a naturally occurring strain of the transmittable disease. Hosts having obtained a naturally occurring strain of the disease have been found to be particularly good sources of antibodies effective in the inventive composition described herein. The avian host can be a host that is actively infected or a host that has been previously infected but did not succumb to the disease.

The sera collected from the avian hosts can be used in the natural form or may be further processed or treated. For example, the sera are preferably treated to substantially remove active forms of the transmittable disease that may be present therein. In one embodiment, polyclonal antibodies are obtained from the serum. Such polyclonal antibodies may be used separate from the serum, used with a separate serum, or reintroduced into the same serum. The polyclonal antibodies can be isolated using a variety of procedures, including chromatography, ammonium sulfate separation, molecular selection protocols, or combinations thereof.

The serum used in a pharmaceutical composition and/or a method of treatment according to the invention preferably exhibits a high neutralization titer for the avian antibodies. In preferred embodiments, the serum contains a high neutralization titer for goose antibodies. As used herein, a neutralization titer is understood to mean a degree of dilution at which a positive detection for a test component may still be found. Titer may be expressed in a variety of dilutions, and the use of a specific dilution in describing the present invention should not be viewed as limiting the invention. By describing the serum as comprising a high neutralization titer of avian antibodies, it is generally meant that the neutralization titer of the serum for the avian antibodies is higher that would be exhibited by the serum under normal conditions. According to one embodiment, normal conditions refers to conditions wherein the serum is obtained from a host that has not been infected with the disease for which antibodies are to be observed. According to another embodiment, the serum neutralization titer can be considered high titer if the neutralization titer is high than would be exhibited if the serum was obtained from a host infected with a non-naturally occurring strain of the disease against which antibodies are to be observed. In one specific embodiment, the neutralization titer of the serum is at least about 1:200. Preferably, the neutralization titer is even higher. For example, in certain embodiment, it is preferable for the neutralization titer of the serum for the avian antibodies to be at least about 1:500, at least about 1:1,000, at least about 1:2,000, at least about 1:3,000, or at least about 1:4,000. In certain embodiments, the neutralization titer for the serum is in the range of 1:320 to 1:8,192, in the range of 1:512 to 1:8,192, in the range of 1:1,024 to 1:8,192, or in the range of 1:2,048 to 1:4,096. Preferably, neutralization titer is evaluated in terms of polyclonal antibodies to the disease to be observed.

Serum neutralization titer for protective antibodies can be a critical factor in the effectiveness of a treatment or prophylactic prepared using the serum. Previous attempts to prepare formulations for treating West Nile Virus have centered on the use of the serum obtained from human hosts. For example, Ben-Nathan et al. (*J Infect Dis*. 2003; 188: 5-12) tested the efficacy of serum obtained from Israeli and U.S. human hosts. They determined that immunoglobulin G (IgG) preparations from Israeli donors had an anti-WNV antibody titer of 1:1600 when evaluated by ELISA. When evaluated by the plaque-reduction test, however, the antibody titer reported for the preparation was >1:80. Preparations made from U.S. blood donors were found to have a titer of only 1:10 when measured by ELISA. One description of a plaque-reduction test is provided by Yang et al., *Journal of Immunological Methods* 276, (2003): 175-183, which is incorporated by reference in its entirety.

In light of these results, it was surprising, according to the present invention, to find that sera obtained from geese exhibited significantly higher neutralization titers for protective antibodies than exhibited by sera obtained from human hosts. Accordingly, compositions and methods of the present invention, which incorporate particularly high neutralization titer sera, would be expected to much more useful for treating and preventing infection by viral diseases, such as West Nile Virus. As one of skill in the art would recognize, neutralization titer is not a property that can be routinely optimized through manipulation. Rather, neutralization titer is a measurement of the neutralizing activity of the antibodies present in the serum. Thus, the requisite neutralization titer either is present or is not, and it is not possible by routine optimization to convert a low neutralization titer serum into a high neutralization titer serum.

Serum exhibiting a high neutralization titer, according to the present invention, against an indigenous transmittable virus can be obtained using a variety of methods that utilize avian hosts, particularly geese. In some embodiments, such a method can comprise exposing geese in an open environment where the animals freely interact with a transmission host and with each other if a population is used. The preferred avian is one that can readily contract the transmittable virus of interest. The transmission host can be another avian capable of passing the disease on to host or can be a separate entity. For example, in the case of West Nile Virus, the transmission host is generally the mosquito. Testing has indicated that polyclonal antibodies can be particularly obtained from a population of avian hosts where at least 3% of the avians previously infected with the viral disease died, or in populations where the animals already showed high neutralization titer to the transmittable virus disease.

It has further been found that utilizing younger hosts for obtaining sera can be more effective, particularly for providing higher neutralization titer sera. For example, when geese are used as the host for obtaining the sera, obtaining sera from goslings rather than breeders has been found effective for obtaining sera with higher neutralization titers for protective antibodies.

Treatment according to the present invention can be carried out on a variety of subjects. In one embodiment, the invention comprises treating or preventing infection by a transmittable viral disease in avian subjects. While such treatment or prevention may be with any avian subject, it is particularly useful with farm-raised avians, such as geese, ducks, turkeys, ostriches, and chickens. Likewise, in other embodiments, the invention is useful in treating or preventing infection by a transmittable viral disease in mammalian subjects. Such mammalian subjects can particularly include humans. In further embodiments, the invention may be used in relation to further mammalian subjects, such as goats, horses, rabbits, rats, mice, pigs, cat, dogs, and the like. In another preferred embodiment, any captive animal, such as exotic zoo animals, may be treated according to the invention prior to or after becoming infected with a transmittable viral disease. In particular, the invention may be carried out with animals where a vaccine is not economically feasible or has not been shown to provide protection.

In light of the above, it becomes particularly clear that the invention is particularly useful in relation to treating or preventing infection in a subject by a transmittable viral disease. In certain embodiments, the present invention provides methods for treating or preventing infection in a subject by administering to the subject goose antibodies (or suitable antibodies derived from another avian host) against the transmittable viral disease. In particular embodiments, the method comprises administering to the subject an amount of a serum effective for treating or preventing infection by a transmittable viral disease, wherein the serum comprises goose antibodies against the transmittable viral disease.

Given the wide range of use associated with the above-noted methods, the administration of the serum can take on a variety of schedules. For example, the administration of the serum could be carried out prior to infection of the subject by the transmittable disease. Such a schedule would be particularly effective in the prevention of infection by the disease. In another embodiment, administration of the serum could be carried out at any point after infection of the subject by the disease. Such a schedule would be particularly effective as a treatment for the disease. When treatment is indicated, such as by evidence of symptoms in the subject common to the given disease, administration of the serum is preferably given until symptoms are no longer evident. One quantifiable symptom is the presence of virus neutralization titer levels in sera collected from the subject corresponding to the viral transmittable disease. Preferably, the treatment according to the invention is effective to reduce the virus neutralization titer levels in the infected subject by 50% or more, and most preferably by at least 90%.

The serum may particularly be administered as part of a pharmaceutical composition. As such, the compositions of the present invention can comprise serum, together with one or more pharmaceutically acceptable carriers therefore, and optionally, other therapeutic ingredients. By "pharmaceutically acceptable carrier" is intended a carrier that is conventionally used in the art to facilitate the storage, administration, and/or the healing effect of the agent. Carriers should be acceptable in that they are compatible with any other ingredients of the composition and not harmful to the recipient thereof A carrier may also reduce any undesirable side effects of the agent. Such carriers are known in the art. See, Wang et al. (1980) *J. Parent. Drug Assn.* 34(6):452-462, herein incorporated by reference in its entirety.

Compositions of the present invention may include short-term, rapid-onset, rapid-offset, controlled release, sustained release, delayed release, and pulsatile release formulations, providing the compositions achieve administration of the serum as described herein. See *Remington's Pharmaceutical Sciences* (18$^{th}$ ed.; Mack Publishing Company, Eaton, Pa., 1990), herein incorporated by reference in its entirety.

Pharmaceutical compositions according to the present invention are suitable for various modes of delivery, including oral, parenteral (including intravenous, intramuscular, subcutaneous, intradermal, and transdermal), and inhalation. The most useful and/or beneficial mode of administration can vary, especially depending upon the condition of the recipient and the disease for which treatment or prevention is desired. In certain embodiment, administration can be by a combination of routes, for example, an initial oral dose followed by a schedule of injections.

The pharmaceutical compositions may be conveniently made available in a unit dosage form, whereby such compositions may be prepared by any of the methods generally known in the pharmaceutical arts. Generally speaking, such methods of preparation comprise combining (by various methods) an active agent, such as the serum comprising avian antibodies, with a suitable carrier or other adjuvant, which may consist of one or more ingredients. The combination of the active ingredient with the one or more adjuvants is then physically treated to present the composition in a suitable form for delivery (e.g. shaping into a tablet or forming an aqueous suspension).

Compositions for parenteral administration include aqueous and non-aqueous sterile injection solutions, which may further contain additional agents, such as anti-oxidants, buffers, bacteriostats, and solutes, which render the compositions isotonic with the blood of the intended recipient. The compositions may include aqueous and non-aqueous sterile suspensions, which contain suspending agents and thickening agents. Such compositions for parenteral administration may be presented in unit-dose or multi-dose containers, such as, for example, sealed ampoules and viles, and may be stores in a freeze-dried (lyophilized) condition requiring only the addition of the sterile liquid carrier, for example, water (for injection), immediately prior to use.

It is contemplated that the serum comprising goose antibodies will be administered to a subject (i.e., an avian or a mammal, preferably a human) in therapeutically effective amounts. That is, in an amount sufficient to effect treatment of a subject already infected by a disease or effect prevention of infection of the subject by the disease. In specific embodiments, an effective amount can be an amount effective to reduce mortality in a population infected by or at risk of infection by the disease. The effective amount of the serum comprising goose antibodies would be expected to vary according to the classification (e.g., avian or mammalian), weight, sex, age, and medical history of the subject. Other factors which influence the effective amount may include, but are not limited to, the severity of the subject's condition, the specific viral disease being treated, and the stability of the serum. Methods to determine efficacy and dosage are known to those skilled in the art. See, for example, Isselbacher et al. (1996) *Harrison's Principles of Internal Medicine* 13 ed., 1814-1882, herein incorporated by reference.

In another embodiment of the invention, the pharmaceutical composition comprising the serum is administered intermittently. By "intermittent administration" is intended administration of a therapeutically effective dose of the serum, followed by a time period of discontinuance, which is then followed by another administration of a therapeutically effective dose, and so forth. Administration of the therapeutically effective dose may be achieved in a continuous manner, as for example with a sustained-release formulation, or it may be achieved according to a desired daily dosage regimen, as for example with one, two, three, or more administrations per day. By "time period of discontinuance" is intended a discontinuing of the continuous sustained-released or daily administration of the serum comprising the avian antibodies. The time period of discontinuance may be longer or shorter than the period of continuous sustained-release or daily administration. During the time period of discontinuance, the antibody level in the subject may fall substantially below the maximum level obtained during the treatment. The preferred length of the discontinuance period depends on the concentration of the effective dose and the form of pharmaceutical composition used. The discontinuance period can be at least 2 days, at least 4 days or at least 1 week. In other embodiments, the period of discontinuance is at least 1 month, 2 months, 3 months, 4 months or greater. When the pharmaceutical composition is used as a vaccine, administration of the serum can be effected through vaccination schedules that may be later determined most effective for achieving a maximum inoculation against a specific transmittable viral disease.

The present invention, in addition to the above useful aspects, also provides a diagnostic kit useful for detecting the presence of a transmittable viral disease in a sample. Generally, the sample will have been obtained from one or more subjects to determine the presence of an active or dormant infection in the subject by a given disease. In one embodiment, the diagnostic kit comprises goose polyclonal antibodies capable of binding to antigens on the viral disease and a detector capable of detecting goose polyclonal antibodies bound to the antigens. The goose polyclonal antibodies used in the diagnostic kit can be obtained as otherwise described herein.

The detector used in the diagnostic kit of the invention can comprise any immunological detection means that use serum, polyclonal antibodies, or antibody fragments as the binding part of the detection. Examples of such methods which would be useful according to the invention include, but are not limited to, ELISA, immunolocalization using tagged antibodies, Western blots, Ouchterlony double diffusion, immunoprecipitation, strip tests, or the like.

EXPERIMENTATION

The present invention is more fully illustrated by the following examples, which illustrate certain embodiments the present invention and are not to be construed as limiting.

Example 1

Preparation of High Neutralization Titer Serum for Viral Protective Bird Antibody Antibody titer measured by serum neutralization (SN) assays were performed to provide analyses of the protective capabilities of the goose antibody to viral infection over traditional ELISA assays that measure binding affinity to viral epitopes. Such traditional methods have shown discrepancies in the past. For example, in studies performed by Ben-Nathan et al. in obtaining antibodies from human subjects, the ELISA titer was reported to be 1:1600; however, the functional protective capabilities were shown to be substantially lower and were actually in the range of 1:80 to 1:320 (*J Infect Dis* 2003; 188: 5-12).

In the present study, geese of a variety of ages were exposed to West Nile Virus, sera were collected from the geese, and the sera of the infected geese were tested using a sera microtiter neutralization plaque assay to measure the usefulness of the sera for protecting cells from viral infection and death. Briefly, a serial 2-fold dilution of goose sera (up to a dilution of 1:8192) were prepared in 96-well microtiter plates and 50 ul PFU of West Nile Virus were added. After incubation at room temperature for 1 hr., $1\times10^4$ Vero cells were added to the mixtures to test for plaque reduction and were incubated for seven days. Plaque reduction neutralizing titers were expressed as the reciprocal of the highest dilution that gave 50% plaque reduction. Experiments indicated that goslings had a significantly higher titer for West Nile Virus antibodies than breeder stock geese, which are used for egg production. In fact, breeder stock geese exhibited a 4 fold lower titer for West Nile Virus antibodies than observed in the younger goslings.

Testing indicated that the sera obtained from the goslings exposed to West Nile Virus had a SN titer of over 4000 by 3 weeks after exposure. The neutralization titer peaked to over 8000 between 35 days to 70 days after exposure and decreased to about 1000 by 90 days after exposure to West Nile Virus. There was no evidence of reduced neutralization titer levels in the ages examined. Surprisingly, in contrast to reports of hyperimmune sera of adult human exposed to West Nile Virus, the neutralization titer of gosling sera was up to 100 fold higher than that observed in human sera (as evidenced by the Ben-Nathan et al. 2003 study referenced above). Accordingly, sera obtained from bird hosts infected with West Nile Virus proved to have much higher neutralization titer for protective antibodies than sera obtained from human hosts.

Actual measured neutralization titer levels in sera collected from goslings infected with West Nile Virus, as described above, are provided below in Table 1. The age of the bird at the time of infection with West Nile Virus and the neutralization titer level at a specified number of days post-infection are provided.

TABLE 1

| Days of Age | Titer Level | Days After Infection | Days of Age | Titer Level | Days After Infection |
|---|---|---|---|---|---|
| 127 | 4,096 | 21 | 127 | >8,192 | 69 |
| 128 | 4,096 | 22 | 121 | 2,048 | 69 |
| 128 | 4,096 | 22 | 127 | 4,096 | 69 |
| 120 | 4,096 | 25 | 125 | 2,048 | 73 |
| 132 | 4,096 | 26 | 132 | 4,096 | 73 |
| 120 | 4,096 | 26 | 120 | 4,096 | 75 |
| 123 | 4,096 | 26 | 125 | 2,048 | 75 |
| 125 | 4,096 | 28 | 120 | 4,096 | 76 |
| 126 | 4,096 | 29 | 126 | 4,096 | 76 |
| 135 | >8,192 | 30 | 126 | 2,048 | 76 |
| 127 | 4,096 | 30 | 126 | 2,048 | 76 |
| 124 | 4,096 | 30 | 103 | 4,096 | 76 |
| 132 | 4,096 | 32 | 133 | 4,096 | 77 |
| 133 | 4,096 | 33 | 135 | 4,096 | 77 |
| 134 | 4,096 | 33 | 127 | 4,096 | 77 |
| 128 | >8,192 | 34 | 128 | 4,096 | 77 |

TABLE 1-continued

| Days of Age | Titer Level | Days After Infection | Days of Age | Titer Level | Days After Infection |
|---|---|---|---|---|---|
| 132 | >8,192 | 39 | 125 | 4,096 | 78 |
| 128 | 4,096 | 40 | 140 | 4,096 | 81 |
| 127 | >8,192 | 46 | 125 | 4,096 | 82 |
| 125 | 4,096 | 51 | 144 | 4,096 | 84 |
| 123 | 4,096 | 52 | 125 | 4,096 | 84 |
| 133 | >8,192 | 52 | 113 | 2,048 | 84 |
| 134 | >8,192 | 53 | 126 | 4,096 | 85 |
| 127 | >8,192 | 53 | 114 | 2,048 | 85 |
| 133 | >8,192 | 54 | 126 | 4,096 | 86 |
| 141 | >8,192 | 60 | 117 | 1,024 | 88 |
| 127 | 4,096 | 64 | 117 | 2,048 | 88 |
| 127 | 4,096 | 65 | 120 | 2,048 | 88 |
| 133 | 4,096 | 66 | 126 | 1,024 | 90 |
| 130 | 4,096 | 66 | 114 | 1,024 | 94 |
| 134 | 4,096 | 67 | 114 | 1,024 | 94 |
| 126 | >8,192 | 68 | 153 | 1,024 | 95 |
| 126 | 4,096 | 68 | | | |

Example 2

Evaluation of Goose Antiserum for Presence of West Nile Virus

Goose antiserum was examined for the presence of West Nile Virus RNA by RT-PCR analysis. DNA was amplified from the prepared RNA in a Perkin-Elmer Model 480 thermal cycler. Primers were designed to map the conserved sequences of the polyprotein gene (West Nile Virus Oligo Detect Kit, WNV Primer Mix [Part No. 5653], Chemicon International, California). The RT-PCR was performed with the QIAGEN one-step RT-PCR kit (QIAGEN, Valencia, Calif.) by using 5 μl of RNA and 0.3 μM of each primer in a 50 μl total reaction volume following the manufacture's protocol. When the PCR mixture was complete, the samples were overlaid with two drops of molecular biology grade mineral oil. All previous manipulations were performed in a Nuaire biological safety cabinet Model NU 425-400. The following cycling times and temperatures were used: cDNA synthesis; 50° C. for 30 minutes, 94° C. for 15 minutes followed by 40 cycles of 94° C. for 1 minute, 57° C. for 30 seconds and 72° C. for 1 minute followed by 72° C. for 15 minutes and 4° C. storage. Following PCR amplification of the DNA samples, the products were separated on 3% submerged agarose gels by electrophoresis. The separated products were visualized by staining with ethidium bromide and electronically photographed using UVP GDS8000 Gel Documentation System (Ultra Violet Products).

Goose antiserum was examined for the presence of West Nile Virus RNA by RT-PCR analysis performed using Chemicon West Nile Virus OLIGODETECT® on antiserum samples. RNA was isolated from goose antisera samples using the QIAamp Viral RNA kit (available from Qiagen) following its suggested protocol. The protocol utilized AVL/carrier RNA addition to sera sample followed by application to a QIAamp spin column. After washing unbound material with AW2, the RNA was eluted using AVE buffer and collected by centrifugation. For RT-PCR analysis West Nile Primer Mix was added in suggested amounts to Qiagen One-Step RT-PCR Enzyme and sample, which included either RNA isolated from antisera or positive control West Nile Virus RNA included in kit. RT-PCR was performed as recommended by kit and subjected to agarose gel analysis.

The positive control West Nile Virus RNA sample exhibited the presence of the appropriate approximately 100 base pair PCR product, however no PCR products were observed in either the negative control or antisera samples. This observation ruled out potential artifacts caused by the presence of West Nile Virus particles in goose antiserum acting as a vaccine rather therapeutic agent.

Example 3

Purification of Goose Antibodies to West Nile Virus

Twenty liters of sera collected from geese infected with West Nile Virus was irradiated for 67 minutes/300 ml aliquots to eliminate any residual virus present in the sera, and the samples were examined by polymerase chain reaction (PCR) to ensure that the sera was virus free. The antibody fraction of the sera was purified by density centrifugation, dialyzed to remove gradient, and concentrated to approximately 3 times the original protein concentration. Purity of the goose antibody was established using RT-PCR analysis. All preparations were greater than 1:4000 determined by a microtiter plaque neutralization assay.

Example 4

Detection of West Nile Virus in Sick Birds using VECTEST®

VECTEST® (Medical Analysis Systems) is recognized by the Center for Disease Control (CDC) as an effective rapid screening test for the detection of West Nile Virus. 39 geese exhibiting advanced West Nile Virus symptoms (e.g., lethargy, staggering, or blindness) were tested for the presence of the virus using VECTEST®. In this "on farm" use, only 5 geese of the 39 geese tested showed a positive VECTEST® response, ranging from +1 to +3 on the test scale. In contrast, the majority of tested geese were found to be positive for West Nile Virus when tested using RT-PCR. Within 7 days, all 5 of the birds testing positive by the VECTEST® died; however, 19 of the 34 birds testing negative by the VECTEST® died within the same period. Accordingly, VECTEST® analyses of serum failed to detect a positive response in most of the birds tested according to the kit instructions.

The brains of selected geese were examined for the presence of West Nile Virus and confirmed to be positive by histopathology for WNV lesions and by molecular PCR diagnostics by the Veterinary Diagnostic Laboratory at the University of Minnesota. The VECTEST® is a monoclonal antibody test based on a Saint Louis Encephalitis antigen panel and appears not to be sufficiently reactive to indigenous West Nile Virus. In contrast, the goose polyclonal antibodies reacted strongly to the indigenous West Nile Virus antigens present in the indigenous population and unexpectedly offer higher reactivity than the monoclonal antibodies used in the VECTEST®.

Example 5

Mortality Rate of Avians Treated with Antiserum Prior to Onset of West Nile Virus Disease Prior to any evidence of increased mortality due to natural infection by West Nile Virus, 6-10 week old goslings were treated by a single subcutaneous injection of 3 milliliters goose antisera according to the invention per gosling. The antisera was negative for West Nile Virus RNA and had a neutralization titer of ≥1:2,000. The antisera treated group included 4705 males and 5095 females. As a control, an untreated group including 5462 males and 7536 females was also evaluated. All animals were continuously exposed to natural infection by the West Nile Virus throughout the course of a six week period.

Deaths among the birds injected with the antisera and the control group was recorded over a 19 day period beginning one day after immunization when the mortality rates became elevated in control group. The percent mortality rates were calculated after first subtracting the average background mortality rate observed in periods when West Nile Virus outbreak was not observed. The percent mortality rate for treated and untreated female and male birds is shown below in Table 2. The overall mortality rate decreased by approximately 60% to 80% in those goslings treated with antiserum. This results show that injection of antiserum can provide an effective control for reducing mortality rates due to West Nile Virus when given prior to onset of a natural outbreak of the disease in a population. RT-PCR analysis of the antiserum for West Nile Virus RNA indicated antibodies residing in the antiserum were effective agents in reducing mortality.

TABLE 2

| Gender | % Mortality in Untreated | % Mortality in Treated | % Reduced Mortality Rate |
|---|---|---|---|
| Male | 5.46 | 1.34 | 75% |
| Female | 2.56 | 1.10 | 57% |

Example 6

Mortality Rate After Onset of West Nile Virus Disease of Avians Treated with Antiserum In another study, goslings showing signs of West Nile Virus infection as judged by a higher mortality were given a single injection subcutaneously with 3 milliliters of goose antisera. The antisera was negative was West Nile Virus RNA and had a neutralization titer level ≥1:2000. The antisera treated group included 2463 males and 2379 females and an untreated control group included 5256 males and 7419 females. Deaths among the injected goslings and the control group were recorded over a 13 day period after the start of injection (such period corresponding to a period when mortality rates were elevated). The percent mortality rates were calculated after first subtracting the average background mortality rate observed in periods when West Nile Virus outbreak was not observed. The percent mortality rate for treated and untreated female and male birds is provided below in Table 3. The overall mortality rate in goslings treated with antiserum was decreased by 57% to 68%. These results show that injection of antiserum, and specific antibodies therein, provided an effective treatment for reducing mortality rates due to West Nile Virus after the natural outbreak of the disease in a population.

TABLE 3

| Gender | % Mortality in Untreated | % Mortality in Treated | % Reduced Mortality Rate |
|---|---|---|---|
| Male | 3.52 | 1.50 | 57% |
| Female | 3.94 | 1.26 | 68% |

Example 7

Evaluation of Prophylaxis Against West Nile Virus in a Large Population of Geese Via Administration of Therapeutic Antibodies to a Subset of the Population It is unclear whether in a goose flock affected by West Nile Virus the disease is spread by transmission via animal to animal in addition to naturally transmission by the original host (i.e., mosquitoes). A study was preformed to determine if the treatment of a sufficient segment of animal population is effective to prevent the spread of the disease within a large population of the entire flock, by potentially either reducing the transmission via animal to animal or reducing the viral pool for mosquitoes. Two sites (approximately 10 miles apart) were selected for testing, both sites being known to have previously had a similar mortality rate in geese due to natural infection by West Nile Virus. At site 1, no geese were treated. At site 2, approximately 65% of the geese were treated with goose sera or antibodies.

WNV was observed at site 1 approximately 10 days prior to first observance at site 2. At site 1, the mortality rate associated with West Nile Virus infection was approximately 13.5% of the population over 25 days. In contrast, at site 2, in antibody treated geese, the mortality rate was 1.56% over the same day period corresponding to an 8 fold decrease in mortality relative to site 1. Surprisingly, in 35% of the geese at site 2 that were not injected with sera, the mortality was also substantially decreased relative to site 1; nevertheless, the mortality rate in untreated geese at site 2 was still higher than those treated with the antibody. This suggests a benefit to untreated animals in a larger population arising from treatment of a subset of the population. Results are shown in Table 4.

TABLE 4

| Treatment | Farm Site | Mortality % | Fold Reduction in Mortality |
|---|---|---|---|
| Untreated | 1 | 13.58% | — |
| Antiserum Treated | 2 | 1.56% | 8.70 |
| Untreated | 2 | 3.02% | 4.39 |

Example 8

Toxicity and Longevity Studies in Mammals of Goose Antibodies to West Nile Virus Ten young adult mice were injected intramuscularly with 0.2 ml purified goose antibodies to West Nile Virus, 10 separate young adult mice were injected intramuscularly with 0.4 ml purified goose anti-WNV antibodies, and 10 separate age-matched control mice were injected intramuscularly with saline. All mice were observed for the first 24 hours and daily for 3 weeks for adverse clinical symptoms including changes in food and water consumption, wasting, and grooming. Neither acute nor chronic symptoms were detected in any of the antibody treated mice.

At 3 weeks post-injection, all 30 of the mice were euthanized and examined for gross anatomical changes with none detected. All spleens and livers were removed and analyzed histologically. No inflammation was noted in any of the experimental mice, and no difference was detected between the antibody treated and control mice. There was no indication that there was any adverse reaction with the introduction of goose antibodies into the mice.

Example 9

Efficacy of Goose Antibodies Against West Nile Virus in Hamsters

To determine if goose antibodies to West Nile Virus would be effective in mammals, the golden hamster model of WNV infection was utilized. The golden hamster model is discussed by Tesh et al., Persistent West Nile Virus Infection in the Golden Hamster: Studins on its Mechanism and Possible Implications for Other Flavivirus Infections, *The Journal of Infectious Diseases* (2005), 192:287-295, and Xiao et al., West Nile Virus Infection in the Golden Hamster (*Mesocricetus auratus*): a Model for West Nile Encephalitis, Emerging Infectious Diseases (2001), 7(4):714-721, both of which are incorporated herein by reference in their entirety.

In the present test, ten hamsters were injected with purified goose antibodies to West Nile Virus, and 10 control hamsters received saline (the day of injection being day 0). On day 1 all 20 hamsters were infected with $10^{3.2}$ PFU (plaque forming units) of WNV-Iowa strain.

The antibody-treated group and the saline group each divided into two groups of five hamsters, the groups being orbitally bled either on days 1 and 3 or days 2 and 4. WNV neutralization titer was determined in 1:5 dilutions of sera. WNV was detectable in the control group by day 1 and increased until the third day when the neutralization titer leveled off (see Table 5 below). Eight of the 10 hamsters from the saline group showed a positive WNV neutralization titer at the level tested. In contrast to the saline treated animals, none of the hamsters receiving the goose antibodies showed any functional virus at the lowest dilution $10^{-1}$.

TABLE 5

| Study Group | Average WNV-Ia Titer/mL | | | |
|---|---|---|---|---|
| | Day 1 | Day 2 | Day 3 | Day 4 |
| Saline Group | | | | |
| Group 1 | $2.01 \times 10^2$ | | $1.67 \times 10^5$ | |
| Group 2 | | $3.34 \times 10^4$ | | $9.19 \times 10^4$ |
| Antibody Treated | | | | |
| Group 1 | ND | | ND | |
| Group 2 | | ND | | ND |

ND—Not Detected

To detect long term effects of the viral infection beyond the four-day test described above, the hamsters were monitored for the next 11 days for clinical signs of West Nile Virus, including lethargy, wasting, and death. The hamsters receiving only saline showed 60% overall mortality over days 4 through 11. Mortality was evidenced by natural death or euthanization in light of viral effects. Complete mortality rates for both groups are shown below in Table 6.

TABLE 6

| Study Group | Died or Euthanized |
|---|---|
| Saline Group | |
| Group 1 | 2/5 |
| Group 2 | 4/5 |

TABLE 6-continued

| Study Group | Died or Euthanized |
|---|---|
| Antibody Treated | |
| Group 1 | 0/5 |
| Group 2 | 0/5 |

As evidenced by the results provided in Table 5 and Table 6, goose antibodies were shown effective for preventing infection by West Nile Virus in mammals Example 10

Preparation of High Neutralization Titer Serum Against Avian Influenza

To test production of therapeutic antibody to avian influenza, an avian influenza virus strain was produced in eggs as a vaccine stock. A stock sample of H3N2 was obtained from ATCC (VR-777) culture collection and used as a viral stock for injection into waterfowl eggs. Two lines, P2SM and JMOP, of goose embryos were used for virus production. Goose embryos at 11 to 17 days of incubation were candled for viability prior to viral injection. Holes were drilled at positions on egg that provided access to either the air sac or chorioallantoic membranes. Approximately 10 to 100 ul of virus stock solution was placed in the air sac or injected into the chorioallantoic membrane. The hole was sealed using glue and returned in the upright position into an incubator. The eggs were monitored for viability by candling.

After 3 to 6 days, approximately 0.5-1.0 ml of allantoic fluid were collected from the allantoic cavity of the goose embryos. RNA was extracted from the samples and analyzed according to the protocol recommended in the RT-PCR kit (available from Qiagen) used for detection of H3N2 virus. Briefly, 500 ul of allantoic fluid were mixed with 500 ul of RLT buffer. From this, 700 ul was applied to a RNeasy column and microfuged for 15 sec and repeated with the remaining sample. 700 ul of Buffer RW1 was applied and the column was microfuged for 15 sec. Next, 500 ul of RPE was similarly applied and microfuged and repeated. To elute bound RNA, 30 to 50 ul of RNase free water was added and microfuged for 15 sec and the sample collected for RT-PCR.

RT-PCR was performed using H3N2 primers obtained from Integrated DNA Technologies, Inc. (Coralville, Iowa). The primer set included a forward primer, M2F, and a reverse primer, M253R. RT PCR was performed according to the Influenza A virus protocol by Fouchier et al. (*J. Clin. Microbiology* 38, 2000), which is incorporated herein by reference. Briefly, RT-PCR conditions were maintained for 30 min at 42° C. and 4 min at 95° C. followed by 40 cycles of 1 min at 95° C., 1 min at 45° C. and 3 min at 72° C. Approximately 15 ul of nucleotide sample was added to a reaction containing 5 ul of each primer and mixed with RT-PCR buffer containing TAQ enzyme and dNTP. Samples of RT-PCR were analyzed by agarose electrophoresis and ethidium bromide staining.

In control eggs (mock injected, or eggs injected with virus but harvested after 3 hours), no virus was detected by the RT-PCR. In contrast, H3N2 virus was found to be produced in 8 of 10 goose embryos. Embryos of both goose strains were shown to produce virus. Highest virus production was exhibited upon injection into the allantoic sac compared to the air sac.

In the event that multiple strains of the transmittable virus are present, two or more strains can be inoculated individually into resistant avian embryos and the allantoic are pooled to provide broader protection to strain variants. For common influenza vaccine typically three predominant strains from the past and/or during the present year are used. After the allantoic fluids are pooled, a number of methods have been used to simplify the recovery of the virus or viral products from the allantoic fluids. Examples of such methods can be found in the following, all of which are incorporated by reference herein: U.S. Pat. Nos. 3,627,873; 4,000,527; 3,316, 153; 4,724,210; and 3,962,421.

The isolated H3N2 influenza viral particles are attenuated by a number of methods to those skilled in the art that inactivate the viral nucleic acid or disrupt key viral coat elements critical in viral infection or a combination of methods. The attenuated viral particles are injected one or more times into goslings for a period sufficient to produce an immune response, typically 3 to 10 weeks. The sera are then harvested from the animals and the sera are tested using a sera microtiter neutralization plaque assay to measure their usefulness in protecting Vero cells from viral infection. Upon demonstrating high neutralization titer goose sera, antibodies are isolated from sera by density centrifugation. The antibodies are dialyzed to remove gradient and are concentrated to approximately 3 times the original protein concentration.

The goose purified antibodies to avian influenza are tested in animals and are found to be effective for preventing infection or preventing or limiting one or more symptoms associated with infection by avian influenza.

Example 11

Generation of High Neutralization Titer Goose Sera Against H1N1 Influenza Virus

The ability of geese to generate a strong antibody response was tested by injection with inactivated H1N1 influenza virus (A/Cal/04/2009). Geese, eight with equal gender diversity, were injected with 500 microliters of a solution of inactivated H1N1 virus and Complete Fruend's adjuvant (1:1 ratio). Each goose received 250 micrograms of inactivated virus. The geese received booster immunizations of the corresponding inactivated virus concentration in Incomplete Fruend's adjuvant at 2, 4, 6, and 8 weeks after the initial injection. The geese were bled prior to the initial immunization and with each subsequent immunization. Immunization elicited a very robust antibody response in all of the geese by week 6 (corresponding to the $3^{rd}$ booster immunization). The response in all geese exceeded 30,000 hemagglutination inhibition assay titers (HA-I). The peak HA-I titers at week 6 (observed in half of the geese tested) were >120,000. Testing thus demonstrated that geese can be induced to generate antibodies to H1N1, a finding that would be expected to extend across the family of influenza viruses. Testing also showed that the anti-influenza antibody response in geese is generated very quickly and reaches exceptionally high titers within a relatively short time after the initial introduction of the virus.

Example 12

Epitope Mapping of Goose-Anti-WNV Antibodies as Evidence of Cross-Family Treatment Ability Viruses in the Flaviviridae family (e.g. West Nile Virus (WNV), dengue virus, and Yellow Fever Virus) are relatively conserved, especially with respect to their non-structural proteins. Testing was carried out to evaluate the possibility that goose antibodies to one member of the Flaviviridae family could provide cross-treatment capability with other members of the same family and to identify characteristics common to the Flaviviridae family indicating that goose antibodies would be expected to provide effective treatments in a significant proportion of the viruses in the family. Epitope-mapping of goose anti-WNV antibodies was carried out using JPT Replitope™ materials (available from JPT Peptide Technologies GmbH, Berlin, Germany). Test results indicated that two epitopes recognized by the IgY from WNV infected geese matched two dengue virus epitopes mapped by other groups. The overlapping WNV epitope and dengue virus epitope were located on their respective non-structural 1 (NS1) proteins (Falconar, A. K., P. R. Young, et al. (1994). "Precise location of sequential dengue virus subcomplex and complex B cell epitopes on the nonstructural-1 glycoprotein." *Arch Virol* 137(3-4): 315-326). Monoclonal antibodies specific for dengue virus NS1 have been shown to be protective against later dengue challenge. The second overlapping epitope between WNV and dengue virus was found on their NS3 proteins. NS3 has a number of enzymatic activities and is considered to be primarily intracellular in both viruses. Despite this, we identified the highest number (i.e., 20) IgY WNV-specific-epitopes on NS3 compared to all proteins assayed, and this showed the strongest binding of all of the IgY epitopes identified on WNV. For dengue virus, NS3 has been identified as mainly having T-cell epitopes—particularly four core NS3 T-cell epitopes (Brinton, M. A., I. Kurane, et al. (1998). "Immune mediated and inherited defenses against flaviviruses." *Clin Diagn Virol* 10(2-3): 129-139). When this data was compared to the results from the WNV sera, not only was NS3 relatively conserved across dengue virus and WNV, but also the epitope that produced the highest median fluorescence intensity (MFI) when bound to IgY overlapped with one of the four strong T-cell epitopes in WNV identified by Brinton et al. This strongly suggests that goose antibodies to WNV may be effective across the entire Flaviviridae family. These results further suggest that the ability of geese to produce antibodies to WNV and the ability of goose anti-WNV antibodies to be an effective treatment in mammals would extend to other members of the Flaviviridae family such that geese would be expected to produce antibodies to other members of the family, and that the produced antibodies would be expected to provide effective treatments in mammals.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of treating a mammal infected with a virus in the Flaviviridae family comprising administering to the infected mammal a composition comprising polyclonal goose antibodies against a virus in the Flaviviridae family, wherein the mammal has not been de-sensitized to goose antibodies prior to said step of administering the composition comprising the polyclonal goose antibodies against the virus in the Flaviviridae family.

2. The method of claim 1, wherein the mammal is selected from the group consisting of goats, horses, rabbits, rats, mice, pigs, and humans.

3. The method of claim 1, wherein the virus infecting the mammal is a flavivirus.

4. The method of claim 1, wherein the flavivirus is selected from the group consisting of Gadgets Gully virus, Kadam virus, Kyasanur Forest disease virus, Langat virus, Omsk hemorrhagic fever virus, Powassan virus, Royal Farm virus, Tick-borne encephalitis virus, Louping ill virus, Meaban virus, Saumarez Reef virus, Tyuleniy virus, Aroa virus, Dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokovera virus, Bagaza virus, Ilheus virus, Israel turkey meningoencephalomyelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, Yellow fever virus, Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, and Rio Bravo virus.

5. The method of claim 1, wherein the composition comprises polyclonal goose antibodies against a virus in the flavivirus genus.

6. The method of claim 5, wherein the virus is selected from the group consisting of Gadgets Gully virus, Kadam virus, Kyasanur Forest disease virus, Langat virus, Omsk hemorrhagic fever virus, Powassan virus, Royal Farm virus, Tick-borne encephalitis virus, Louping ill virus, Meaban virus, Saumarez Reef virus, Tyuleniy virus, Aroa virus, Dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokovera virus, Bagaza virus, Ilheus virus, Israel turkey meningoencephalomyelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, Yellow fever virus, Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, and Rio Bravo virus.

7. The method of claim 1, wherein the virus that the polyclonal goose antibodies are against is the same virus infecting the mammal.

8. The method of claim 1, wherein the virus that the polyclonal goose antibodies are against is different from the virus infecting the mammal.

9. The method of claim 1, wherein said treating comprises preventing or limiting one or more symptoms associated with infection by the virus.

10. The method of claim 1, wherein the composition is derived from a serum that exhibits a neutralization titer of at least about 1:200 when evaluated according to a plaque reduction test.

11. The method of claim 10, wherein the serum exhibits a neutralization titer of at least about 1:500 when evaluated according to a plaque reduction test.

12. The method of claim 10, wherein the serum exhibits a neutralization titer of at least about 1:1000 when evaluated according to a plaque reduction test.

13. The method of claim 1, wherein said administering comprises a route of administration selected from the group consisting of injection, inhalation, oral administration, and combinations thereof.

* * * * *